United States Patent
Weiner et al.

(10) Patent No.: US 9,024,088 B1
(45) Date of Patent: May 5, 2015

(54) HYDROGENATION CATALYSTS COMPRISING A MIXED OXIDE COMPRISING NICKEL

(71) Applicant: Celanese International Corporation, Irving, TX (US)

(72) Inventors: Heiko Weiner, Pasadena, TX (US); Zhenhua Zhou, Houston, TX (US); Victor J. Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 14/263,332

(22) Filed: Apr. 28, 2014

(51) Int. Cl.
C07C 29/149 (2006.01)

(52) U.S. Cl.
CPC .................................. C07C 29/149 (2013.01)

(58) Field of Classification Search
USPC ......................................... 568/885, 913, 918
See application file for complete search history.

(56) References Cited

U.S. PATENT DOCUMENTS

| | | |
|---|---|---|
| 4,398,039 A | 8/1983 | Pesa et al. |
| 4,517,391 A | 5/1985 | Schuster et al. |
| 4,613,700 A | 9/1986 | Maki et al. |
| 4,777,303 A | 10/1988 | Kitson et al. |
| 4,804,791 A | 2/1989 | Kitson et al. |
| 4,918,248 A | 4/1990 | Hattori et al. |
| 5,149,680 A | 9/1992 | Kitson et al. |
| 5,306,845 A | 4/1994 | Yokohama et al. |
| 6,204,417 B1 | 3/2001 | Fischer et al. |
| 6,495,730 B1 | 12/2002 | Konishi et al. |
| 6,509,180 B1 | 1/2003 | Verser et al. |
| 6,521,565 B1 | 2/2003 | Clavenna et al. |
| 7,608,744 B1 | 10/2009 | Johnston et al. |
| 7,851,404 B2 | 12/2010 | Lok |
| 7,863,489 B2 | 1/2011 | Johnston et al. |
| 7,884,253 B2 | 2/2011 | Stites et al. |
| 7,923,405 B2 | 4/2011 | Kharas et al. |
| 8,017,544 B2 | 9/2011 | Casci et al. |
| 8,309,772 B2 | 11/2012 | Weiner et al. |
| 8,329,961 B2 | 12/2012 | Danjo et al. |
| 8,471,075 B2 | 6/2013 | Johnston et al. |
| 8,536,236 B2 | 9/2013 | Lok et al. |
| 8,546,622 B2 | 10/2013 | Jevtic et al. |
| 8,680,321 B2 | 3/2014 | Johnston et al. |
| 2009/0088317 A1 | 4/2009 | Frye, Jr. et al. |
| 2011/0060169 A1 | 3/2011 | Kaizik et al. |
| 2013/0178661 A1 | 7/2013 | Zhou et al. |
| 2013/0178663 A1 | 7/2013 | Zhou et al. |
| 2013/0178664 A1 | 7/2013 | Zhou et al. |
| 2013/0178670 A1 | 7/2013 | Zhou et al. |

FOREIGN PATENT DOCUMENTS

| | | |
|---|---|---|
| CN | 102139234 | 8/2011 |
| CN | 202214306 | 5/2012 |
| CN | 102513120 | 6/2012 |
| CN | 102600842 | 7/2012 |
| CN | 102658165 | 9/2012 |
| CN | 102671682 | 9/2012 |
| CN | 102688768 | 9/2012 |
| CN | 102690171 | 9/2012 |
| CN | 102757308 | 10/2012 |
| CN | 102847535 | 1/2013 |
| CN | 102847544 | 1/2013 |
| CN | 102941097 | 2/2013 |
| CN | 102941108 | 2/2013 |
| CN | 103055956 | 4/2013 |
| CN | 103084186 | 5/2013 |
| CN | 103772143 | 5/2014 |
| CN | 103785412 | 5/2014 |
| CN | 103785414 | 5/2014 |
| CN | 103785416 | 5/2014 |
| CN | 103785417 | 5/2014 |
| CN | 103785418 | 5/2014 |
| CN | 103787827 | 5/2014 |
| CN | 103787829 | 5/2014 |
| CN | 103787830 | 5/2014 |
| EP | 0091027 | 10/1983 |
| EP | 0175558 | 3/1986 |
| EP | 0191995 | 8/1986 |
| JP | 2001-046874 | 2/2001 |
| WO | WO 2013/054303 | 1/2013 |

OTHER PUBLICATIONS

Castro-Grijalba, et al., "Preparation and Characterization of Catalysts Based on Cassiterite (SnO2) and it's Application in Hydrogenation of Methyl Esters", The Journal of the Argentine Chemical Society, vol. 98, 2011, pp. 48-59.

*Primary Examiner* — Sikarl Witherspoon

(57) ABSTRACT

A process is disclosed for producing ethanol comprising contacting acetic acid and hydrogen in a reactor in the presence of a catalyst comprising a binder and a mixed oxide comprising nickel and tin.

20 Claims, No Drawings

US 9,024,088 B1

HYDROGENATION CATALYSTS COMPRISING A MIXED OXIDE COMPRISING NICKEL

FIELD OF THE INVENTION

The present invention relates generally to processes for hydrogenating acetic acid to form ethanol and to novel catalysts comprising a mixed oxide comprising nickel for use in such processes and catalyst preparation thereof.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced.

As an alternative to fermentation, ethanol may be produced by hydrogenating acetic acid and esters thereof. Ethanol production via the reduction of acetic acid generally uses a hydrogenation catalyst. The reduction of various carboxylic acids over metal oxides has been proposed.

EP0175558 describes the vapor phase formation of carboxylic acid alcohols and/or esters such as ethanol and ethyl acetate from the corresponding mono and di-functional carboxylic acid, such as acetic acid, in the presence of a copper oxide-metal oxide supported catalyst, such as $CuO/ZnAl_2O_4$. A disadvantage with copper oxide catalysts in carboxylic acid hydrogenation reactions is the lack of long-term catalyst stability.

U.S. Pat. No. 4,398,039 describes a process for the vapor phase hydrogenation of carboxylic acids to yield their corresponding alcohols in the presence of steam and a catalyst comprising the mixed oxides of ruthenium, at least one of cobalt, nickel, and optionally one of cadmium, zinc, copper, iron, rhodium, palladium, osmium, iridium and platinum. The total loading of active metals is 5%. A process is further provided for the preparation of carboxylic acid esters from carboxylic acids in the absence of steam utilizing the above-identified catalysts.

U.S. Pat. No. 4,517,391 describes preparing ethanol by hydrogenating acetic acid under superatmospheric pressure and at elevated temperatures by a process wherein a predominantly cobalt-containing catalyst is used and acetic acid and hydrogen are passed through the reactor, at from 210 to 330° C., and under 10 to 350 bar, under conditions such that a liquid phase is not formed during the process.

U.S. Pat. No. 4,918,248 describes producing an alcohol by catalytically reducing an organic carboxylic acid ester with hydrogen in the presence of a catalyst obtained by reducing a catalyst precursor comprising (A) copper oxide and (B) titanium oxide and/or titanium hydroxide at a weight ratio of (A) to (B) in the range between 15/85 and 65/35. The component (A) may alternatively be a composite metal oxide comprising copper oxide and up to 20 wt. % of zinc oxide.

Other hydrogenation catalysts that are not metal oxides have also been proposed. These catalysts typically include a precious metal. U.S. Pat. No. 7,608,744 describes a process for the selective production of ethanol by vapor phase reaction of acetic acid at a temperature of about 250° C. over a hydrogenating catalyst composition either cobalt and palladium supported on graphite or cobalt and platinum supported on silica selectively produces ethanol. U.S. Pat. No. 7,863,489 describes a process for the selective production of ethanol by vapor phase reaction of acetic acid over a platinum and tin supported on silica, graphite, calcium silicate or silica-alumina hydrogenation catalyst and in a vapor phase at a temperature of about 250° C. U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes the production of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another production process of alcohols by the hydrogenation of carboxylic acids in the presence of a catalyst comprising a noble metal of Group VIII and rhenium.

Thus, further improvements to hydrogenation catalysts that demonstrate high stability, conversion of acetic acid and selectivity to ethanol are needed. In addition, it would be useful to have an efficient catalyst that does not require precious metals.

SUMMARY OF THE INVENTION

In a first embodiment of the present invention, there is provided a process for producing ethanol, comprising contacting acetic acid and hydrogen in a reactor in the presence of a catalyst comprising a binder, and a mixed oxide comprising nickel and tin. The mixed oxide is present in an amount from 20 to 90 wt. %, e.g., from 50 to 85 wt. %, based on the total weight of the catalyst. The mixed oxide loading is determined prior to reducing any of the metals of the mixed oxide. The total nickel loading of the catalyst may be from 25 to 80 wt. %, e.g., from 40 to 70 wt. %, based on the metal content of the catalyst. The total tin loading of the catalyst is from 30 to 70 wt. %, e.g. from 40 to 55 wt. %, based on the total metal content of the catalyst. The catalyst may have a molar ratio of nickel to tin from 0.5:1 to 2:1. In one embodiment, the mixed oxide may further comprise cobalt. The total cobalt loading of the catalyst is from 30 to 60 wt. %, based on the metal content of the catalyst. In another embodiment, the catalyst of the present invention may be substantially free of precious metals such as rhenium, ruthenium, rhodium, palladium, osmium, iridium, and platinum, including combinations thereof. In another embodiment, the catalyst of the present invention may be substantially free of zinc, zirconium, cadmium, copper, manganese, and molybdenum. The binder is selected from the group consisting of silica, aluminum oxide, and titania. The binder loading may be from 5 to 40 wt. %, e.g., 10 to 20 wt. %, based on the total weight of the catalyst.

The contacting of the catalyst comprising the mixed oxide with acetic acid may be performed in a vapor phase at a temperature of 200° C. to 350° C., an absolute pressure of 101 kPa to 3000 kPa, and a hydrogen to acetic acid mole ratio of greater than 4:1. In one embodiment, the catalyst comprising the mixed oxide may be contacted with a mixed stream comprising from 50 to 95 wt. % acetic acid and from 5 to 50 wt. % ethyl acetate.

In a second embodiment of the present invention, there is provided a process for producing ethanol, comprising contacting acetic acid and hydrogen in a reactor in the presence of a catalyst comprising a binder, and a mixed oxide comprising nickel, wherein the total nickel loading of the catalyst is from 25 to 80 wt. %, based on the metal content of the catalyst. The mixed oxide may further comprise tin. In addition, the catalyst may be substantially free of zinc, zirconium, cadmium, copper, manganese, and molybdenum.

In a third embodiment of the present invention, there is provided a catalyst comprising a binder, and a mixed oxide comprising nickel and tin. The mixed oxide is present in an amount from 20 to 90 wt. %, e.g., from 50 to 85 wt. %, based on the total weight of the catalyst. The binder is selected from the group consisting of silica, aluminum oxide, and titania. The binder loading may be from 5 to 40 wt. %, e.g., 10 to 20 wt. %, based on the total weight of the catalyst.

In a fourth embodiment of the present invention, there is provided a catalyst comprising a binder, and a mixed oxide comprising nickel, wherein the total nickel loading of the catalyst is from 25 to 80 wt. %, e.g., from 40 to 70 wt. %, based on the metal content of the catalyst. The binder is selected from the group consisting of silica, aluminum oxide, and titania. The binder loading may be from 5 to 40 wt. %, e.g., 10 to 20 wt. %, based on the total weight of the catalyst. The mixed oxide may further comprise tin. The total tin loading of the catalyst is from 30 to 70 wt. %, e.g. from 40 to 55 wt. %, based on the total metal content of the catalyst.

DETAILED DESCRIPTION OF THE INVENTION

The present invention relates to processes for producing ethanol by hydrogenating acetic acid in the presence of a catalyst comprising a binder and a mixed oxide comprising nickel. A mixed oxide refers to an oxide having cations of more than one chemical element. For purposes of the present invention, mixed oxides include the reduced metals of the mixed oxide. In one embodiment of the present invention, the catalyst may comprise a mixed oxide comprising nickel and tin. In another embodiment, the catalyst may comprise a mixed oxide comprising nickel, tin, and cobalt. The catalyst may also comprise a binder, such as an inert material. Silica may be a preferred binder. The catalysts comprising a mixed oxide of nickel and tin demonstrate an advantageous conversion of acetic acid to ethanol at high selectivities. This allows the catalysts of the present invention to be used in several processes for producing ethanol.

The catalysts comprising a mixed oxide of nickel and tin demonstrate an advantageous conversion of acetic acid to ethanol at high selectivities with low ethyl acetate formation and other by-product formation, in particular diethyl ether. Low byproduct formation reduces the separation requirements to obtain ethanol. This allows the catalysts of the present invention to be used in several processes for producing ethanol.

In one embodiment, the catalyst may comprise a binder and a mixed oxide comprising nickel and tin, wherein the mixed oxide is present in an amount from 20 to 90 wt. %, based on the total weight of the catalyst. Unless otherwise stated, all ranges disclosed herein include both endpoints and all numbers between the endpoints. This amount is determined prior to reducing any of the metals of the mixed oxide. More preferably, the mixed oxide may be present in an amount from 50 to 85 wt. %, based on the total weight of the catalyst. The catalysts of the present invention have a higher loading of active metals, such as at least 40 wt. % active metals, e.g., Ni and Sn, based on the total weight of the catalyst, e.g., at least 45 wt. % or at least 50 wt. %. The total nickel loading of the catalyst may be from 25 to 80 wt. %, e.g., from 40 to 70 wt. %, based on the total metal content of the catalyst. The total tin loading of the catalyst may be from 30 to 70 wt. %, e.g., from 40 to 60 wt. %, based on the total metal content of the catalyst. Lower loadings of nickel and tin of less than 20 wt. % are to be avoided since this decreases the conversion of acetic acid and/or selectivity to ethanol.

The catalysts of the present invention have been found to be effective when the mixed oxide has a molar ratio of nickel to tin that is from 0.5:1 to 2:1, e.g., from 0.75:1 to 2:1, or from 1.1:1 to 1.4:1. Without being bound by theory, a molar excess of nickel may improve the selectivity to ethanol in the catalyst. The mixed oxide may have the formula:

wherein x is from 0 to 0.5, e.g., from 0.1 to 0.4 or from 0.1 to 0.25, and z is may equal to or less than 3+2x. In one embodiment, z is equal to 3+2x. Preferably z is greater than 1.

Without being bound by theory, nickel and tin are predominately present on the catalyst as a mixed oxide, such as nickel(II)-stannate. However, the catalyst may contain some discrete regions of nickel oxide and tin oxide. In addition, the metallic nickel or tin, i.e. reduced metal, may also be present on the catalyst. The mixed oxide, and thus catalyst, is preferable anhydrous.

The binder of the catalyst may be an inert material which is used to enhance the crush strength of the final catalyst. The binder is preferably stable under the hydrogenation conditions. Suitable inert materials comprise silica, aluminum oxide, and titania. The binder may be present in an amount from 5 to 40 wt. %, e.g. from 10 to 30 wt. % or from 10 to 20 wt. %, based on the total weight of the catalyst. Thus, in one embodiment, the catalyst may comprise a silica binder and a mixed oxide comprising nickel and tin, which is substantially free of precious metals.

In one embodiment, in addition to nickel and tin, the mixed oxide may further comprise cobalt. The total cobalt loading of the catalyst may be from 30 to 60 wt. %, e.g., 40 to 50 wt. %, based on the total metal content of the catalyst. Lower amounts of cobalt may also be used when used in combination with nickel and tin. Without being bound by theory, cobalt may improve the activity of the catalysts to be more selective to ethanol. In addition, cobalt may be useful for decreasing conversion of acetic to other oxygenates, such as ethyl acetate.

In one embodiment, the mixed oxide may comprise other promoter metals, which may include precious metals. These promoter metals may be present in relatively small amounts from 0 to 10 wt. %, e.g., from 0.01 to 3 wt. %. The promoter metals may include titanium, vanadium, chromium, manganese, iron, copper, zinc, zirconium, molybdenum, tungsten, cadmium, rhenium, ruthenium, rhodium, palladium, osmium, iridium, or platinum.

In other embodiments, to reduce the cost of the catalyst, the catalyst, including the mixed oxide, of the present invention may be substantially free of precious metals, selected from the group consisting of rhenium, ruthenium, rhodium, palladium, osmium, iridium, or platinum. Substantially free means that the catalyst does not contain precious metals beyond trace amounts of less than 0.0001 wt. %. To avoid introducing precious metals into the catalysts of the present invention, it is preferred than no precursors containing precious metals are used during the catalyst preparation.

In other embodiments, the mixed oxide may be substantially free of non-precious promoter metals, such as, zinc, zirconium, cadmium, copper, manganese, and/or molybdenum, including combinations thereof. When the mixed oxide is substantially free of these non-precious promoter metals, it is preferred that the binder, and thus catalyst are also substantially free of these non-precious promoter metals. Thus, in one embodiment, the catalyst may comprise a silica binder and a mixed oxide comprising nickel and tin, and may be preferably substantially free of promoter metals, including precious metals.

The surface area of the catalyst comprising a mixed oxide comprising nickel may be from 100 to 250 $m^2/g$, e.g., from 150 to 180 $m^2/g$. Pore volumes are between 0.18 and 0.35 mL/g, with average pore diameters from 6 to 8 nm. The morphology of the catalyst may be pellets, extrudates, spheres, spray dried microspheres, rings, pentarings, trilobes, quadrilobes, multi-lobal shapes, or flakes. The shape of the catalyst may be determined by hydrogen process conditions to provide a shape that can withstand pressure drops in the reactor.

The catalyst comprising a binder and a mixed oxide of the present invention has an on-stream stability for at least 50 hours, e.g., at least 200 hours, at constant reaction conditions. Stability refers to a catalyst that has a change of less than 2% in conversion and less than 2% selectivity to ethanol, after initial break-in. In addition, stability refers to a catalyst that does not demonstrate any increase in by-product formation while on-stream. This greatly improves the industrial usefulness of a catalyst for continuous production. Also, this reduces the need to change the catalyst and reduces reactor down time for continuous processes.

The catalyst comprising a mixed oxide of the present invention may be made by the following method. Other suitable methods may also be used in conjunction with the present invention. In one embodiment, two solutions containing a metal precursor are prepared. Suitable metal precursors may include metal halides, metal halide hydrates, metal acetates, metal hydroxyls, metal oxalates, metal nitrates, metal alkoxides, metal sulfates, metal carboxylates and metal carbonates.

For purposes of the present invention, there is at least one precursor comprising nickel and at least one precursor comprising tin. The precursors may be prepared in the same solution or in different solutions. Each solution may be an aqueous solution that comprises water. In some embodiments, when the mixed oxide comprises a molar excess of nickel, at least one of the solutions may comprise an alkali hydroxide, such as sodium hydroxide. The solutions are combined and a binder, preferably in solid form, is added thereto while mixing. When a halide precursor is used, the mixture may be filtered and washed to remove halide anions. The mixed solution may be aged for a sufficient period of time at a temperature from 5° C. to 60° C., e.g., from 15° C. to 40° C. To obtain an anhydrous catalyst, the mixture may be dried at a temperature from 50° C. to 150° C., e.g. from 75° C. to 125° C., for 1 to 24 hours. Next, the material may be calcined in air at a temperature from 300° C. to 700° C., e.g., from 400° C. to 600° C., for 0.5 to 12 hours.

When additional metals, such as cobalt or another promoter metal disclosed herein, are included in the catalyst, a metal precursor thereto may be added to either the nickel precursor solution or the tin precursor solution. In some embodiments, a separate solution may be prepared and combined once the nickel precursor solution and the tin precursor solution are combined.

In one embodiment, the present invention comprises a method of making a catalyst comprising a binder and a mixed oxide comprising nickel and tin, the method comprising preparing a first solution comprising water and a nickel precursor, wherein the nickel precursor is selected from the group consisting of nickel halides, nickel halide hydrates, nickel acetates, nickel hydroxyls, nickel oxalates, nickel nitrates, nickel alkoxides, nickel sulfates, nickel carboxylates and nickel carbonates, and preparing a second solution comprising water, sodium hydroxide, and a tin precursor, wherein the tin precursor is selected from the group consisting of tin halides, tin halide hydrates, tin acetates, tin hydroxyls, tin oxide dispersion (such as ammonia, amine dispersed dispersion or hydrated dispersion), tin oxalates, tin nitrates, tin alkoxides, tin sulfates, tin carboxylates and tin carbonates. The second solution is added to the first solution and then silica gel is added, in solid form, to the mixture with stirring. The mixture may be dried and calcined to form a catalyst comprising a binder and a mixed oxide comprising nickel and tin of the present invention.

The hydrogenation reaction of a carboxylic acid, acetic acid in this example, may be represented as follows:

$$HOAc + 2H_2 \rightarrow EtOH + H_2O$$

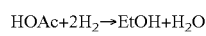

It has surprisingly and unexpectedly been discovered that the catalysts of the present invention provide high conversion of acetic acid and high selectivities to ethanol, when employed in the hydrogenation of carboxylic acids such as acetic acid. Embodiments of the present invention beneficially may be used in industrial applications to produce ethanol on an economically feasible scale.

The feed stream to the hydrogenation process preferably comprises acetic acid. In some embodiments, pure acetic acid may be used as the feed. In other embodiments, the feed stream may contain some other oxygenates, such as ethyl acetate, acetaldehyde, or diethyl acetal, or higher acids, such as propanoic acid or butanoic acid. Minor amounts of ethanol may also be present in the feed stream. In one embodiment, the feed stream may comprise from 50 to 95 wt. % acetic acid, and from 5 to 50 wt. % oxygenates. More preferably, the feed stream may comprise from 60 to 95 wt. % acetic acid and from 5 to 40 wt. % ethyl acetate. The other oxygenates may originate from recycle streams that are fed to the hydrogenation reactor. In other embodiments, the feed stream may comprise from 0 to 15 wt. % water, e.g., from 0.1 to 10 wt. % water. An exemplary feed stream, e.g., a mixed feed stream, may comprise from 50 to 95 wt. % acetic acid, from 5 to 50 wt. % ethyl acetate, from 0.01 to 10 wt. % acetaldehyde, from 0.01 to 10 wt. % ethanol, and from 0.01 to 10 wt. % diethyl acetal.

The process of hydrogenating acetic acid to form ethanol according to one embodiment of the invention may be conducted in a variety of configurations using a fixed bed reactor or a fluidized had reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may range from 200° C. to 350° C., e.g., from 200° C. to 325° C., from 225° C. to 300° C., or from 250° C. to 300° C. The pressure may range from 101 kPa to 3000 kPa (about 1 to 30 atmospheres), e.g., from 101 kPa to 2700 kPa, or from 101 kPa to 2300 kPa. The reactants may be fed to the reactor at a gas hourly space velocities (GHSV) of greater than 500 hr$^{-1}$, e.g., greater than 1000 hr$^{-1}$, greater than 2500 hr$^{-1}$ and even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 8000 hr$^{-1}$.

In another aspect of the process of this invention, the hydrogenation is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 8000 hr$^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 12:1 to 1:1. Most preferably, the molar ratio of hydrogen to acetic acid is equal to or greater than 4:1, e.g., greater than 5:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 40 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using catalysts and processes of the present invention may achieve favorable conversion of acetic acid and favorable selectivity and productivity to ethanol. For purposes of the present invention, the term conversion refers to the amount of acetic acid in the feed that is converted to a compound other than acetic acid. Conversion is expressed as a mole percentage based on acetic acid in the feed.

The conversion of acetic acid (AcOH) is calculated from gas chromatography (GC) data using the following equation:

$$\text{AcOH Conv.(\%)} = 100 * \frac{\text{mmol AcOH (feed stream)} - \text{mmol AcOH (product)}}{\text{mmol AcOH (feed stream)}}$$

For purposes of the present invention, the conversion may be at least 50%, e.g., at least 60% or at least 70%. In some embodiments, the catalysts of the present invention may achieve these high conversions without precious metals, such as rhenium, ruthenium, palladium, platinum, rhodium, and iridium.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from GC data using the following equation:

$$\text{EtOH Sel. (\%)} = 100 * \frac{\text{mmol EtOH (product)}}{(\text{mmol Converted\_AcOH}) + 2*(\text{mmol Converted\_EtAc})}$$

This equation is used when ethyl acetate is present in the feed stream and there is conversion on ethyl acetate. If pure acid is used as feed, the equation can be simplified to the following equation:

$$\text{EtOH Sel. (\%)} = 100 * \frac{\text{mmol EtOH (product)}}{\text{mmol AcOH (feed stream)} - \text{mmol AcOH (product)}}$$

For purposes of the present invention, the selectivity to ethanol of the catalyst is at least 40%, e.g., at least 50% or at least 65%. In some embodiments, the catalysts of the present invention may achieve this high selectivity to ethanol without precious metals. The selectivity to ethyl acetate, acetaldehyde and/or diethyl acetate is preferable less than the selectivity to ethanol, and may be less than 50%, e.g., less than 45% or less than 40%. In one embodiment of the present invention, it is also desirable to have low selectivity to undesirable products, such as methane, ethane, and carbon dioxide. The selectivity to these undesirable products is less than 5%, e.g., less than 3% or less than 1.5%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel. In addition, the selectivity to diethyl ether should be low, less than 5%, e.g. less than 3% or less than 1%.

Productivity refers to the grams of a specified product, e.g., ethanol, formed during the hydrogenation based on the kilogram of catalyst used per hour. In one embodiment of the present invention, a productivity of at least 200 grams of ethanol per kilogram catalyst per hour, e.g., at least 400 grams of ethanol or least 600 grams of ethanol, is preferred. In terms of ranges, the productivity preferably is from 200 to 4,000 grams of ethanol per kilogram catalyst per hour, e.g., from 400 to 3,500 or from 600 to 3,000.

In another embodiment, the invention is to a crude ethanol product formed by processes of the present invention. The crude ethanol product produced by the hydrogenation process of the present invention, before any subsequent processing, such as purification and separation, typically will comprise primarily unreacted acetic acid and ethanol. In some exemplary embodiments, the crude ethanol product comprises ethanol in an amount from 15 to 70 wt. %, e.g., from 20 wt. % to 60 wt. %, or from 25 wt. % to 55 wt. %, based on the total weight of the crude ethanol product. The crude ethanol product typically will further comprise unreacted acetic acid, depending on conversion, and water as shown in Table 1. The amount of ethyl acetate, acetaldehyde, and diethyl acetal may vary. The others may include alkanes, ethers, other acids and esters, other alcohols, etc. The alcohols may be n-propanol and iso-propanol. Exemplary crude ethanol compositional ranges, excluding hydrogen and other non-condensable gases, in various embodiments of the invention are provided below in Table 1.

TABLE 1

CRUDE ETHANOL PRODUCT COMPOSITIONS

| Component | Conc. (wt. %) | Conc. (wt. %) | Conc. (wt. %) |
| --- | --- | --- | --- |
| Ethanol | 25 to 70 | 30 to 65 | 40 to 65 |
| Acetic Acid | 0 to 30 | 0.1 to 20 | 0.5 to 10 |
| Ethyl Acetate | 0 to 20 | 0.1 to 15 | 1 to 10 |
| Acetaldehyde | 0 to 10 | 0.1 to 5 | 0.5 to 2 |
| Diethyl Acetal | 0 to 10 | 0.1 to 5 | 0.5 to 1 |
| Water | 5 to 35 | 5 to 30 | 5 to 25 |
| Other | 0 to 10 | 0 to 5 | 0 to 1 |

An ethanol product may be recovered from the crude ethanol product produced by the reactor using the catalyst of the present invention using several different techniques, such as distillation columns, adsorption units, membranes, or molecular sieves. For example, multiple columns may be used to remove impurities and concentration ethanol to an industrial grade ethanol or an anhydrous ethanol suitable for fuel applications. Exemplary separation and recovery processes are disclosed in U.S. Pat. Nos. 8,309,773; 8,304,586; and 8,304,587; and U.S. Pub. Nos. 2012/0010438; 2012/0277490; and 2012/0277497, the entire contents and disclosure of which are hereby incorporated by reference.

In one embodiment, the process, including separation, may comprise hydrogenating an acetic acid feed stream in a reactor in the presence of a catalyst comprising a binder and mixed oxide comprising nickel and tin to form a crude ethanol product, separating at least a portion of the crude ethanol product in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, wherein the second column is an extractive distillation column, feeding an extraction agent to the second column, and separating at least a portion of the second residue in a third column into a third distillate comprising ethanol and a third residue comprising water. Water from the third residue may be used as the extraction agent. Also, a fourth column may be used to separate acetaldehyde from the second distillate.

In another embodiment, the process, including separation, may comprising hydrogenating acetic acid and/or an ester thereof in a reactor in the presence of a catalyst comprising a binder and mixed oxide comprising nickel and tin to form a crude ethanol product, separating a portion of the crude ethanol product in a first distillation column to yield a first distillate comprising acetaldehyde and ethyl acetate, and a first residue comprising ethanol, acetic acid, ethyl acetate and water, separating a portion of the first residue in a second distillation column to yield a second residue comprising acetic acid and an vapor overhead comprising ethanol, ethyl acetate and water, removing water, using a membrane or pressure swing absorption, from at least a portion of the vapor overhead to yield an ethanol mixture stream having a lower water content than the at least a portion of the vapor overhead, and separating at least a portion of the ethanol mixture stream in a third distillation column to yield a third distillate comprising ethyl acetate and a third residue comprising ethanol and less than 8 wt. % water.

The raw materials used in connection with the process of this invention may be derived from any suitable source including natural gas, petroleum, coal, biomass and so forth. It is well known to produce acetic acid through methanol carbonylation, acetaldehyde oxidation, ethane oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352 the disclosure of which is incorporated herein by reference, for example, teaches a method of retrofitting a methanol plant for the manufacture of acetic acid. By retrofitting a methanol plant, the large capital costs associated with CO generation for anew acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111, which discloses a process for converting waste biomass through gasification into synthesis gas as well as U.S. Pat. No. 6,685,754, the disclosures of which are incorporated herein by reference.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

In one embodiment, the process may comprise a process for the formation of ethanol comprising, converting a carbon source into acetic acid, and contacting a feed stream containing the acetic acid and hydrogen with a catalyst comprising a binder and a mixed oxide comprising nickel and tin of the present invention. In another embodiment, the process may comprise a process for the formation of ethanol comprising converting a carbon source, such as biomass, into a first stream comprising syngas, catalytically converting at least some of the syngas into a second stream comprising methanol, separating some of the syngas into hydrogen and carbon monoxide, catalytically converting at least some of the methanol with some of the carbon monoxide into a third stream comprising acetic acid; and reducing at least some of the acetic acid with some of the hydrogen in the presence of a catalyst comprising a binder and a mixed oxide comprising nickel and tin of the present invention into a fourth stream comprising ethanol.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. Any known dehydration catalyst, such as zeolite catalysts or phosphotungstic acid catalysts, can be employed to dehydrate ethanol to ethylene, as described in copending U.S. Pub. Nos. 2010/0030002 and 2010/0030001 and WO2010146332, the entire contents and disclosures of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

The catalysts of the present invention may be used with one or more other hydrogenation catalysts in a stacked bed reactor or in a multiple reactor configuration. A stacked bed reactor is particular useful when one catalyst is suitable for high selectivity to ethanol at low conversions. The catalyst comprising the mixed oxide of the present invention may be used in combination with another hydrogenation catalyst to increase the acetic acid conversion and thus improve the overall yield to ethanol. In other embodiments, the catalyst comprising the mixed oxide of the present invention may be used to convert unreacted acetic acid in a recycle stream.

In one embodiment, the catalyst comprising the mixed oxide of the present invention may be used in the second reactor bed of a stacked bed configuration. The first reactor bed may comprise a different hydrogenation catalyst. Suitable hydrogenation catalysts are described in U.S. Pat. Nos. 7,608,744; 7,863,489; 8,080,694; 8,309,772; 8,338,650; 8,350,886; 8,471,075; 8,501,652 and US Pub. Nos. 2013/0178661; 2013/0178663; 2013/0178664; the entire contents and disclosure of which are hereby incorporated by reference. In general, the different hydrogenation catalyst in the first bed may comprise a Group VIII metal and at least one promoter metal on a supported catalyst. Suitable Group VIII metals may include rhodium, rhenium, ruthenium, platinum, palladium, osmium, and iridium. Suitable promoter metals may include copper, iron, cobalt, vanadium, nickel, titanium, zinc, chromium, molybdenum, tungsten, tin, lanthanum, cerium, and manganese. Combinations of Pt/Sn, Pt/Co, Pd/Sn, Pt/Co, and Pd/Co may be preferred for the different catalyst. The metal loadings may be from 0.1 to 20 wt. %, e.g., from 0.5 to 10 wt. %, based on the total weight of the catalyst. The support may be any suitable support such as silica, alumina, titania, silica/alumina, pyrogenic silica, silica gel, high purity silica, zirconia, carbon (e.g., carbon black or activated carbon) zeolites and mixtures thereof. The supported catalyst may comprise a modified support that changes the acidity or basicity of the support. The support modified may be present in an amount from 0.5 to 30 wt. %, e.g., from 1 to 15 wt. %, based on the total weight of the catalyst. Acidic modifiers may include tungsten, molybdenum, vanadium, or oxides thereof. Suitable basic modifiers may include magnesium or calcium, such as calcium metasilicate.

The first bed may operate under similar hydrogenation conditions as the mixed oxide catalyst of the present invention. The reaction temperature of the first bed may range from 200° C. to 350° C., e.g., from 250° C. to 300° C. The pressure may range from 101 kPa to 3000 kPa, e.g., from 101 kPa to 2300 kPa. The reactants may be fed to the reactor at a gas hourly space velocities (GHSV) of greater than 500 hr$^{-1}$, e.g., greater than 1000 hr$^{-1}$. In one embodiment, fresh hydrogen may be fed to the first bed and the unreacted hydrogen from the first bed is passed along to the second bed with the reaction effluent. In other embodiments, each bed may receive a fresh hydrogen feed.

Exemplary catalysts for the first reactor bed may comprise one or more the following catalysts. One exemplary catalyst comprises 0.1 to 3 wt. % platinum and 0.5 to 10 wt. % tin on a silica support having from 5 to 20 wt. % calcium metasilicate. Another exemplary catalyst comprises 0.1 to 3 wt. % platinum and 0.5 to 10 wt. % tin on a silica support having from 5 to 20 wt. % calcium metasilicate and from 0.5 to 10 wt. % cobalt. Another exemplary catalyst comprises 0.1 to 3 wt. % platinum, 0.5 to 10 wt. % tin, and 0.5 to 10 wt. % cobalt on a silica support having from 5 to 20 wt. % tungsten. Another exemplary catalyst comprises 0.1 to 3 wt. % platinum and 0.5 to 10 wt. % tin on a silica support having from 5 to 20 wt. % tungsten, and 0.5 to 10 wt. % cobalt. Another exemplary catalyst comprises 0.1 to 3 wt. % platinum, 0.5 to 10 wt. % tin, and 0.5 to 10 wt. % cobalt on a silica support having from 5 to 20 wt. % tungsten, 0.5 to 10 wt. % tin, and 0.5 to 10 wt. % cobalt.

In one embodiment, the stack bed process may comprise introducing a feed stream of acetic acid and hydrogen into a stacked bed reactor that comprises a first bed and a second bed to produce a crude ethanol product, wherein the first bed comprises a first catalyst comprising platinum and tin on a first support and the second bed comprises a second catalyst comprising a binder and a mixed oxide comprising nickel and tin of the present invention, recovering ethanol from the crude ethanol product in one or more columns. The acetic acid feed stream may comprise from 5 to 50 wt. % ethyl acetate and from 50 to 95 wt. % acetic acid.

Various other combinations of hydrogenation catalyst may be readily employed with the catalyst comprising the mixed oxide of the present invention. In addition, the order of the catalyst beds in the stack bed configuration may be arranged as needed to achieve ethanol production at high yields.

In addition, the catalyst comprising the mixed oxide of the present invention may be used in a first reactor with a copper containing catalyst in a second reactor that is suitable for converting ethyl acetate to ethanol. The second reactor may comprise a second catalyst that comprises copper or an oxide thereof. In one embodiment, the second catalyst may further comprise zinc, aluminum, chromium, cobalt, or oxides thereof. A copper-zinc or copper-chromium catalyst may particular preferred. Copper may be present in an amount from 35 to 70 wt. % and more preferably 40 to 65 wt. %. Zinc or chromium may be present in an amount from 15 to 40 wt. % and more preferably 20 to 30 wt. %.

The second bed that contains a copper catalyst may operate with a reaction temperature from 125° C. to 350° C., e.g., from 180° C. to 345° C., from 225° C. to 310° C., or from 290° C. to 305° C. The pressure may range from 101 kPa to 3000 kPa, e.g., from 700 to 8,500 kPa, e.g., from 1,500 to 7,000 kPa, or from 2,000 to 6,500 kPa. The reactants may be fed to the reactor at a gas hourly space velocities (GHSV) of greater than 500 hr$^{-1}$, e.g., greater than 1000 hr$^{-1}$, greater than 2500 hr$^{-1}$ and even greater than 5000 hr$^{-1}$.

In another embodiment, the stack bed process may comprise introducing a feed stream of acetic acid and hydrogen into a stacked bed reactor that comprises a first bed and a second bed to produce a crude ethanol product, wherein the first bed comprises a first catalyst comprising a binder and a mixed oxide comprising nickel and tin of the present invention and the second bed comprises a second catalyst comprising copper-containing catalyst of the present invention, recovering ethanol from the crude ethanol product in one or more columns. The acetic acid feed stream may comprise from 5 to 50 wt. % ethyl acetate and from 50 to 95 wt. % acetic acid.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

Example 1

An aqueous solution of nickel(II) nitrate hexahydrate was prepared by dissolving 23.73 g (0.082 mol) in about 150 mL of deionized H$_2$O. Separately, an aqueous solution of sodium stannate was prepared by dissolving 21.765 g (0.0816 mol) in about 150 mL of deionized H$_2$O. The sodium stannate solution was then added to the nickel solution using a drop funnel over 10 minutes with stirring (10-12 mL/min) at room temperature. Next, 4.6 g of SiO$_2$ (silica gel, solid) was added to the mixture with stirring, and it was then aged with stirring for 2 hrs at room temperature. The mixture was then aged with stirring for 2 hrs at room temperature. The material was then collected on a Buchner funnel (Watman #541 filter paper), and washed with deionized H$_2$O to remove the sodium chloride. The filtrate was periodically tested for Cl$^-$ (using Ag$^+$ solution). Approximately 1 L of deionized H$_2$O was used until no more chloride could be detected. The solid was then transferred into a porcelain dish, and dried overnight at 120° C. under circulating air. Yield: about 21.6 g of the dried nickel-tin hydroxo precursor. In order to obtain the anhydrous catalyst comprising nickel(II) stannate, NiSnO$_3$, the material was calcined at 500° C. under air for 6 hrs using a heating rate of 3 degree/min. The catalyst contains 80 wt. % of the mixed oxide and is represented by the formula [SiO$_2$—NiSnO$_3$ (80)].

Example 2

The catalysts of Example 1 and several other comparative catalysts were tested under the following conditions. The comparative examples used a different metal than nickel and generally followed a similar preparation as Example 1. The results are shown in Table 2.

A test unit having four independent tubular fixed bed reactor systems with common temperature control, pressure and gas and liquid feeds. The reactors are made of ⅜" 316 SS tubing (0.95 cm), and are 12⅛" (30.8 cm) in length. The vaporizers are also made of ⅜" 316 SS tubing, and are 12⅜" (31.4 cm) in length. The reactors, vaporizers, and their respective effluent transfer lines are electrically heated. The reactor effluents are routed to chilled water condensers and knock-out pots. Condensed liquids are collected automatically, and then manually drained from knock-out pots as needed. Non-condensed gases are passed through a manual back pressure regulator and then scrubbed through water and vented to the fume hood. A volume of 8 to 10 mL of catalyst (3 mm pellets or 8-10 mesh) is loaded to reactor. Both inlet and outlet of reactor are filled with glass beads (3 mm) to form the fixed bed. The following running conditions for catalyst screening were used: [HOAc], 0.092 g/mL; [H$_2$], 342 sccm ([H$_2$]/[HOAc]=9.5); T=280° C.; p=300 psig (2170 kPa); 8 or 10 mL of heterogeneous catalyst (3 mm pellets or 8-10 mesh); GHSV=2,268 or 2,835 H$^{-1}$, 24-200 hrs of reaction time. The conversion and selectivity was measured at 48 hours.

TABLE 2

| Catalysts | HOAc Conversion | EtOH | EtOAc | Selectivity AcH | Acetal | Others |
|---|---|---|---|---|---|---|
| Present Invention | | | | | | |
| [SiO$_2$—NiSnO$_3$(80)] | 58% | 51% | 36% | 6% | 6% | 0.15% |
| Comparative Examples | | | | | | |
| [SiO$_2$—ZnSnO$_3$(80)] | 7% | 4% | 65% | 16% | 0% | 15.37% |
| [SiO$_2$—MnSnO$_3$(80)] | 4% | 3% | 47% | 18% | 0% | 31.65% |
| [SiO$_2$—CuSnO$_3$(80)] | 5% | 4% | 41% | 22% | 0% | 32.35% |
| [SiO$_2$—FeSnO$_3$(80)] | 11% | 1% | 14% | 8% | 0% | 76.44% |

As compared to other mixed oxides, the mixed oxide comprising nickel and tin demonstrate significant improvements in terms of conversion of acetic acid and selectivity to ethanol.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol comprising contacting acetic acid and hydrogen in a reactor in the presence of a catalyst comprising a binder, and a mixed oxide comprising nickel and tin.

2. The process of claim 1, wherein the mixed oxide is present in an amount from 20 to 90 wt. %, based on the total weight of the catalyst.

3. The process of claim 1, wherein the mixed oxide is present in an amount from 50 to 85 wt. %, based on the total weight of the catalyst.

4. The process of claim 1, wherein the total nickel loading of the catalyst is from 25 to 80 wt. %, based on the metal content of the catalyst.

5. The process of claim 1, wherein the total nickel loading of the catalyst is from 40 to 70 wt. %, based on the total metal content of the catalyst.

6. The process of claim 1, wherein the total tin loading of the catalyst is from 30 to 70 wt. %, based on the total metal content of the catalyst.

7. The process of claim 1, wherein the total tin loading of the catalyst is from 40 to 55 wt. %, based on the total metal content of the catalyst.

8. The process of claim 1, wherein the catalyst has a molar ratio of nickel to tin from 0.5:1 to 2:1.

9. The process of claim 1, wherein the mixed oxide further comprises cobalt.

10. The process of claim 9, wherein the total cobalt loading of the catalyst is from 30 to 60 wt. %, based on the metal content of the catalyst.

11. The process of claim 1, wherein the catalyst is substantially free of rhenium, ruthenium, rhodium, palladium, osmium, iridium, and platinum.

12. The process of claim 1, wherein the catalyst is substantially free of zinc, zirconium, cadmium, copper, manganese, and molybdenum.

13. The process of claim 1, wherein the binder comprises silica, aluminum oxide, and titania.

14. The process of claim 1, wherein the binder is present in an amount from 5 to 40 wt. %, based on the total weight of the catalyst.

15. The process of claim 1, wherein the binder is present in an amount from 10 to 20 wt. %, based on the total weight of the catalyst.

16. The process of claim 1, wherein the mixed oxide catalyst has a surface area from 100 to 250 $m^2/g$.

17. The process of claim 1, wherein the contacting is performed in a vapor phase at a temperature of 200° C. to 350° C., an absolute pressure of 101 kPa to 3000 kPa, and a hydrogen to acetic acid mole ratio of equal to or greater than 4:1.

18. A process for producing ethanol comprising contacting acetic acid and hydrogen in a reactor in the presence of a catalyst comprising a binder, and a mixed oxide comprising nickel, wherein the total nickel loading of the catalyst is from 25 to 80 wt. %, based on the metal content of the catalyst.

19. The process of claim 18, wherein the mixed oxide further comprises tin.

20. The process of claim 18, wherein the catalyst is substantially free of zinc, zirconium, cadmium, copper, manganese, and molybdenum.

* * * * *